United States Patent
Phillips et al.

(10) Patent No.: US 6,436,041 B1
(45) Date of Patent: Aug. 20, 2002

(54) MEDICAL ULTRASONIC IMAGING METHOD WITH IMPROVED ULTRASONIC CONTRAST AGENT SPECIFICITY

(75) Inventors: Patrick J. Phillips, Sunnyvale; Ismayil M. Guracar, Redwood City, both of CA (US)

(73) Assignee: Acuson Corporation, Mountain View, CA (US)

( * ) Notice: Subject to any disclaimer, the term of this patent is extended or adjusted under 35 U.S.C. 154(b) by 59 days.

(21) Appl. No.: 09/746,690

(22) Filed: Dec. 22, 2000

(51) Int. Cl.$^7$ ................................. A61B 8/00
(52) U.S. Cl. ........................ 600/437; 600/458
(58) Field of Search ................ 600/437, 442–447, 600/458; 73/625, 626; 367/7, 11, 130, 138

(56) References Cited

U.S. PATENT DOCUMENTS

| | | |
|---|---|---|
| 5,577,505 A | 11/1996 | Brock-Fisher et al. |
| 5,632,277 A | 5/1997 | Chapman et al. |
| 5,706,819 A | 1/1998 | Hwang et al. |
| 5,951,478 A | 9/1999 | Hwang et al. |
| 6,095,980 A | 8/2000 | Burns et al. |
| 6,251,074 B1 * | 6/2001 | Averkiou et al. ........... 600/447 |
| 6,283,919 B1 * | 9/2001 | Roundhill et al. .......... 600/447 |
| 6,340,348 B1 * | 1/2002 | Krishnan et al. ........... 600/447 |

OTHER PUBLICATIONS

Higher Order Nonlinear Ultrasonic Imaging, 1999 IEEE International Ultrasonics Symposium, Oct. 17–20, Nevada, USA.

U.S. Ser. No. 09/514,803.
U.S. Ser. No. 09/650,942.

* cited by examiner

Primary Examiner—Marvin M. Lateef
Assistant Examiner—Ali M. Imam

(57) ABSTRACT

An improved method for suppressing fundamental or desired harmonic orders in an ultrasonic medical imaging system transmits at least one reverberation-suppression pulse prior to the transmission of a multiple-pulse sequence. Receive signals associated with the pulses of the multiple-pulse sequence are acquired and combined using receive weights selected to suppress energy at either the fundamental or a desired harmonic of the fundamental.

12 Claims, 2 Drawing Sheets

MEDICAL ULTRASONIC IMAGING METHOD WITH IMPROVED ULTRASONIC CONTRAST AGENT SPECIFICITY

BACKGROUND

This invention relates to medical ultrasonic imaging methods using multiple-pulse sequences, and in particular to improvements to such imaging methods that improve contrast agent specificity.

As described below, the use of multiple transmit events to insonify a single direction is a preferred method for detecting harmonics of ultrasonic contrast agents. The incorporation of unequal amplitudes and/or phases between pulses within a sequence of two or more pulses has been used to suppress fundamental signal energy and to retain other order harmonics of the fundamental signal when the two or more receive pulses are combined properly. Adequate fundamental signal suppression provides improved contrast-to-tissue specificity, since tissue image clutter, or haze, is minimized and harmonics specific to the contrast agents are detected and displayed against a tissue background that is dark due to the lack of significant fundamental signals.

Acoustic reverberations can degrade the amount of fundamental signal suppression obtained with a multiple-pulse sequence for detecting contrast agents. Reverberant energy detected after a single transmit event that originated from an earlier transmit event can perturb the signal strengths of one or more of the received pulses such that the combination of multiple received pulses will not adequately suppress the fundamental signal energy.

More specifically, a number of multiple-pulse techniques have been introduced in the last few years that improve the detectability of ultrasonic contrast agents. The initial techniques simply used RF or I/Q filtering on a single receive pulse and only required a single transmit event. More advanced techniques combined this single-pulse filtering, or the lack of any filtering, with two or more pulses fired in the same direction. These techniques improve contrast agent specificity by using the multiple-pulse combinations to isolate a desired harmonic signal rather than relying solely on the RF filtering on each received pulse. This multiple-pulse approach offers improved signal bandwidth and improved spatial resolution, since harmonics of interest can overlap in the frequency domain with fundamental signals. The use of very broad single-pulse RF filters, or the lack of any RF filtering, retains the overlapping signal spectra, thereby preserving signal bandwidths. The multiple-pulse approaches also provide the potential to suppress other harmonics including the fundamental signal, while preserving a specific harmonic of interest. These techniques can also reject multiple harmonic orders including the fundamental, while preserving desired harmonics.

Prior multiple-pulse techniques that alter the transmit amplitude and/or phase between two or more transmit events for the purposes of detecting ultrasonic contrast agents include the following:

1. Pulse Inversion (U.S. Pat. Nos. 5,706,819 and 5,951,478) and Phase Inversion (U.S. Pat. No. 5,632,277)

These techniques do not vary the transmit amplitude between two firings, but transmit the opposite polarity on the second firing. With the summation of the two received pulses, fundamental signals as well as all odd order harmonics are suppressed while second order signals are retained.

2. Pulse Inversion Doppler (or Power Pulse Inversion) (U.S. Pat. No. 6,095,980)

This technique is an extension of Pulse Inversion that incorporates three or more transmit events where the amplitude does not change between firings but the polarity alternates between transmit firings. With properly selected receive weights, a combination of multiple receive pulses suppresses all odd order harmonics and retains second order signals. The use of additional transmit events and receive weights offers the potential for improved tissue flash suppression and improved contrast signal to electronic noise levels.

3. "Means for Increasing Sensitivity in Non-linear Ultrasound Imaging Systems" (U.S. Pat. No. 5,577,505)

This technique does not vary the transmit phase between two or more transmit events but varies the amplitude between transmit events. The weights, or scaling, on each received pulse are chosen such that the fundamental signals are suppressed and second harmonic signals are retained when all the received pulses are combined.

4. "Higher Order Nonlinear Ultrasonic Imaging" 1999 IEEE International Ultrasonics Symposium, October 17–20, Nevada, USA, Session: Non-linear Imaging, page 188 of Technical Program and Abstracts.

This technique varies transmit amplitudes and phases and chooses the appropriate receive weights to specifically isolate a single harmonic order.

5. "Medical Diagnostic Ultrasound System Using Contrast Pulse Sequence Imaging" (U.S. patent application Ser. No. 09/514,803) and "Medical Ultrasonic Imaging Pulse Transmission Method" (U.S. patent application Ser. No. 09/650,942)

These techniques also vary the transmit amplitudes and phases between two or more transmit events to preferentially isolate single harmonic orders or two or more harmonic orders.

All these techniques use the idea of varying the transmit phase and/or amplitude between two or more pulses, but are susceptible to sub-optimal fundamental cancellation resulting from acoustic reverberations.

SUMMARY

The methods described below transmit an additional pulse or pulses before the desired multiple-pulse sequence or incorporates modifications to a desired transmit pulse sequence across different scan lines such that the combination of received pulses exhibits improved fundamental signal suppression. The additional transmit pulse(s) are selected with the appropriate amplitude and phase to enhance fundamental signal suppression. For desired pulse sequences that are modified on a line-by-line basis, specific amplitudes and phases are chosen to properly suppress acoustic reverberations. This method can use any multiple-pulse sequence that varies the amplitude and/or phase between any two transmit pulses to achieve improved agent-to-tissue specificity and improved image quality when using ultrasonic contrast agents.

DETAILED DESCRIPTION OF THE PRESENTLY PREFERRED EMBODIMENTS

This section describes two methods to improve the suppression of acoustic reverberations in multiple-pulse imaging of the type which varies amplitude and/or phase between at least two transmit pulses of the sequence. The first method transmits additional pulses before the desired multiple-pulse sequence. The second method modifies the desired sequence from line-to-line while maintaining frame rates. Both methods use the general approach shown in FIG. 2, which will be described first.

Figure 1:
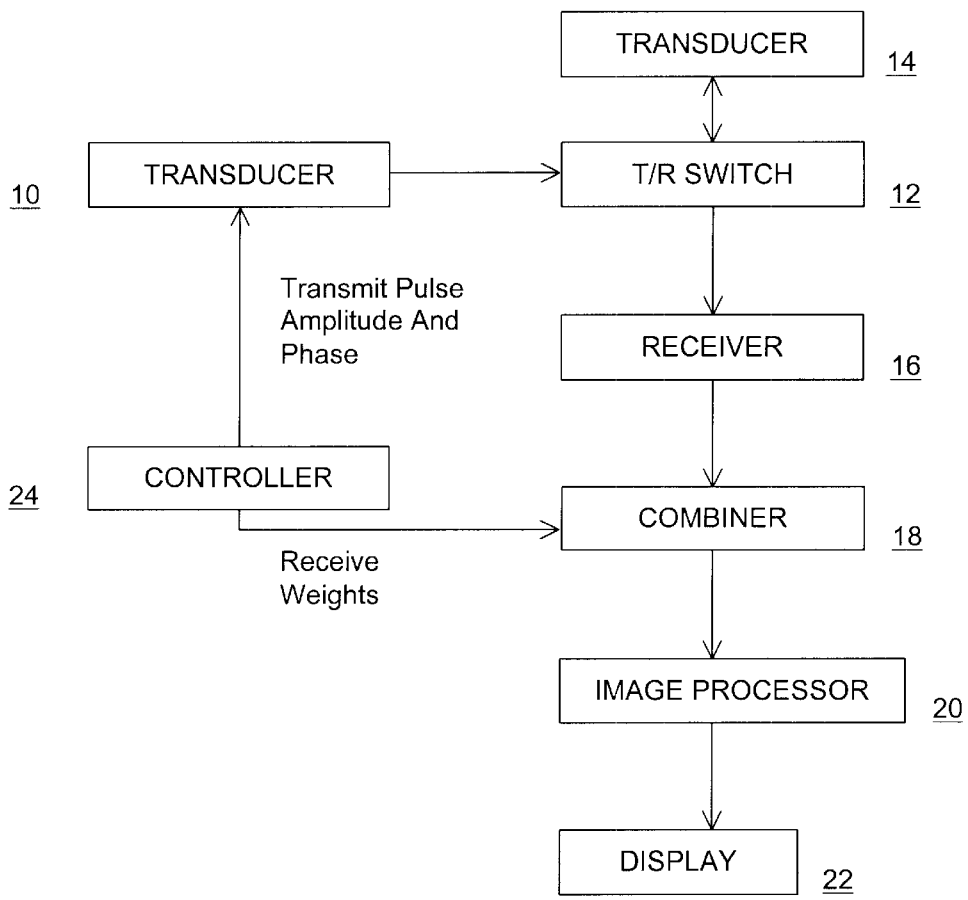
FIG. 1 is a block diagram of a medical diagnostic imaging system.
Figure 2:
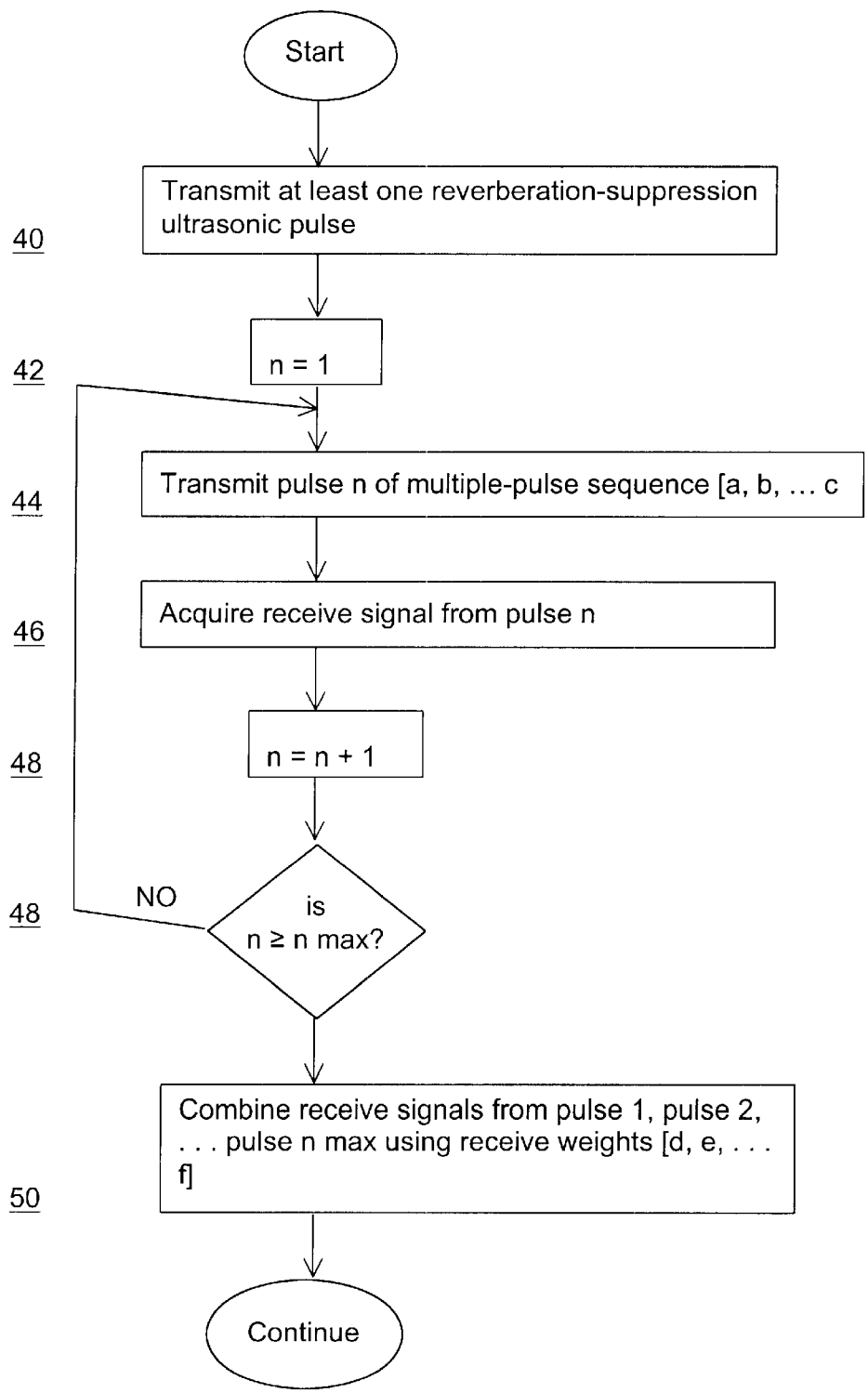
FIG. 2 is a flowchart of a method implemented by the system of FIG. 1.

FIGS. 1 and 2

FIG. 1 shows a schematic representation of a medical ultrasonic imaging system suitable for use in implementing the method of this invention. The system of FIG. 1 includes a transmitter 10 that generates transmit signals that are applied via a transmit/receive switch 12 to a transducer 14. The transducer 14 generates ultrasonic transmit pulses in response to the signals from the transmitter 10 and receives ultrasonic echo signals in response to these pulses. These echo signals are passed via the transmit/receive switch 12 to a receiver 16. The receiver 16 may include a receive beamformer when the transducer 14 includes an array of transducer elements, and the receiver 16 generates receive signals that are applied to a combiner 18. The combined image signals generated by the combiner 18 are applied to an image processor 20, and the output of the image processor 20 is displayed on a display 22.

As described in greater detail below in conjunction with FIG. 2, the transmitter 10 is controlled by a controller 24 such that the transmit pulses are arranged in multiple-pulse sequences. The transmit pulses within an given multiple-pulse sequence include at least two transmit pulses that differ in at least one of amplitude and phase. Similarly, the controller 24 applies receive weights to the combiner 18. The combiner 18 combines the receive signals associated with a given multiple-pulse sequence of transmit pulses, using appropriate receive weights. In general, the receive weights and the transmit pulse amplitudes and phases are chosen such that the combined signal generated by the combiner 18 suppresses desired components including selected order harmonic components and/or fundamental components in the combined signal.

The number of pulses in the multiple-pulse sequence and the selection of amplitude and phase for individual pulses within a multiple-pulse sequence can vary widely, depending upon the application. In general, any suitable multiple-pulse sequence can be used, including all of those disclosed in the documents cited in the background portion of this specification. Similarly, any suitable set of receive weights can be used, including all of the receive weights disclosed in the documents cited in the background portion of this specification.

In general, any suitable hardware can be used to implement the present invention, and the various components of FIG. 1 can be implemented in many ways. The transmitter and receiver can use analog hardware, dedicated digital hardware, or programmable digital hardware to perform the desired actions. The transducer 14 can include a phased array of transducer elements, or it can alternatively include one or more mechanically steered elements. Any suitable techniques can be used to implement the functions of the combiner 18 and the image processor 20. Simply by way of example, the hardware described in U.S. patent applications Ser. Nos. 09/514,803 and 09/650,942 (assigned to the Assignee of the present invention and hereby incorporated by reference) can be used.

FIG. 2 shows in general terms a method in accordance with this invention. As shown in FIG. 2, first at least one reverberation-suppression ultrasonic pulse is transmitted in block 40. Then a multiple-pulse sequence of ultrasonic pulses is transmitted and associated receive signals acquired in blocks 42–48. The multiple-pulse sequence can include as few as two transmit pulses or three, four, five or more transmit pulses. After receive signals from all of the transmit pulses of the desired multiple-pulse sequence have been acquired, these receive signals are combined in block 50 using desired receive weights. The amplitude and phase of the reverberation-suppression ultrasonic pulse 40 is selected to enhance the desired cancellation achieved by the combining act of block 50.

In some embodiments, the reverberation-suppression ultrasonic pulse of block 40 may be steered in the same direction as the multiple-pulse sequence of blocks 42–48. In other embodiments, the reverberation-suppression ultrasonic pulse of block 40 may be steered along a different direction, typically along an adjacent ultrasonic line. In this case, the reverberation-suppression ultrasonic pulse may be included as the last pulse or pulses of an additional multiple-pulse sequence, steered along the adjacent acoustic line.

With this general introduction, two specific methods for implementing the general method of FIG. 2 will now be described.

Method 1:

This method will first be introduced by an example and then described in more general terms.

Additional Pulses

Consider the example of a three transmit pulse sequence [1 2 1], where each number represents the peak amplitude for a respective transmit pulse of arbitrary shape, and all of the pulses are steered along a common direction or acoustic line. The corresponding receive weights of this example are [1 −1 1]. The sum, or combination, $(1\times1)+(2\times-1)+(1\times1)$ yields zero and represents perfect suppression of linear echoes from the fundamental frequency (assuming there is no motion between the received pulses). For second order scattering from contrast agents (assuming a simple pressure squared relationship) the combination $(1\times1)+(4\times-1)+(1\times1)$ produces a non-zero number representing detected second harmonic energy. For third order scattering (assuming a simple cubed relationship) the combination $(1\times1)+(8\times-1)+(1\times1)$ is also non-zero, representing detected third order harmonic energy that may appear at three times the fundamental frequency or at the fundamental frequency (here called cubic fundamental).

If acoustic reverberations are seen after a given transmit event that originated from a previous transmit event, fundamental signal energy from these acoustic reverberations will not cancel in the combination discussed above. During the time period when the three pulses above are received, acoustic reverberations would appear as $A(0)+A(1)+A(2)$, where A represents a scaling factor due the strength of the reverberations and the 0 represents the initial lack of any reverberation since the first transmit pulse was not preceded by any transmit pulses. When these reverberations exist they are also weighted by the receive weights [1 −1 1] and embedded within the combination of three received pulses. In this example, the combination $A(0\times1)+A(1\times-1)+A(2\times1)$ is not zero. This unwanted residual fundamental energy shows up in the image as image clutter, or haze, and reduces the agent-to-tissue specificity.

Adequate suppression of acoustic reverberations can be obtained by transmitting a reverberation-suppression pulse with a value of −1 immediately prior to the first transmit pulse of the sequence at one pulse repetition interval (PRI) before the first pulse of the sequence is transmitted. With this extra pulse, the reverberant acoustic field will generate a combination $A(-1\times1)+A(1\times-1)+A(2\times1)$, which is equal to zero.

This simple example is just one example of a general approach to determining the proper amplitude and phase of one or more additional transmit pulses for suppressing acoustic reverberations. Generally, for a three-pulse sequence the following equation can be used to solve for the reverberation-suppression transmit pulse Z:

$$(Z \times R1) + (T1 \times R2) + (T2 \times R3) = 0, \quad (Eq\ 1)$$

where T1 and T2 are the first and second transmit pulses from the desired transmit pulse sequence T1, T2, and T3, respectively, and R1, R2, and R3 are the corresponding receive weights.

Solving for Z, we obtain:

$$Z = -(T1 \times R2 + T2 \times R3)/R1. \quad (Eq\ 2)$$

This general concept can easily be extended to pulse sequences of two transmit events or more than three transmit events, and to sequences or clinical applications that benefit from more than one reverberation-suppression pulse that precedes a desired pulse sequence. As one example, corresponding to the three-pulse sequence above, the additional pulses Z2 and Z1 operative to suppress acoustic reverberations can be chosen as follows:

$$Z = Z \text{(from above example and transmitted after } Z2\text{)}, \quad (Eq\ 3)$$

$$Z2 = (-T1 \times R3)/R1 + ((T1R2 \times R2) + (T2 \times R2 \times R3))/(R1 \times R1). \quad (Eq\ 4)$$

Examples of multiple-pulse sequences and preferred reverberation-suppression transmit pulses which precede the multiple-pulse sequence include the following. The reverberation-suppression pulses are shown in boldface type in Table 1. This table is not limiting but used for illustration.

sequence to reduce transmitted pressures. The use of a smaller number of elements during one transmit event than is used for another transmit event can be effective at generating reduced incident pressure at the contrast agent site while still maintaining constant peak transmit voltages among all transmit events. This approach minimizes variable deleterious transmit nonlinearities between different transmit events that can be difficult to compensate for when different transmit voltages are used. See U.S. patent application Ser. No. 09/650,942 for a discussion of subaperture selection.

The subaperture is preferably optimized for the additional transmit pulse(s) preceding the multiple-pulse sequence to contribute to optimal suppression of fundamental acoustic reverberations. Again, by using an example, this concept will be described. Consider a three-pulse sequence which breaks up a full aperture into two subapertures. Each subaperture has at least one less element than the full aperture. For example, one subaperture may be ⅓ the full aperture, while the other is ⅔ the full aperture; or each subaperture may be half the full aperture, but with different transducer elements used for each subaperture. To optimally suppress fundamental acoustic reverberations, the proper subaperture is preferably used for the additional, reverberation-suppression transmit pulses. Consider the three-pulse sequence $$(T1a \times R1) + ((T2a + T2b) \times R2) + (T3b \times R3) = 0, \quad (Eq\ 5)$$

where T1a represents subaperture a which is fired first, T2a and T2b represent subapertures a and b, respectively, which are fired second and simultaneously, and T3b represents subaperture b which is fired third. Receive weights R1, R2, and R3 correspond, respectively, to the ordering of the transmit events. For this sequence a single additional pulse preferably satisfies Equation 6:

$$Z = ((Tb-1) \times R2 - R3)/R1. \quad (Eq\ 6)$$

TABLE 1

| Multiple-Pulse Sequence | Improved Sequence | Number of Additional Pulses |
|---|---|---|
| [1 0.5] × [1 −2] | [2 1 0.5] × [1 −2] | one |
| [1 −1 1] × [1 2 1] | [−1 1 −1 1] × [1 2 1] | one |
| [1 −2 1] × [1 1 1] | [1 1 −2 1] × [1 1 1] | one |
| [1 2 1] × [1 1 1] | [−1 1 2 1] × [1 −1 1] | one |
| [1 −2 1] × [1 1 1] | [−2 1 1 −2 1] × [1 1 1] | two |
| [1 2 1] × [1 −1 1] | [−2 −1 1 2 1] × [1 −2 1] | two |
| [0.5 −1 1 −0.5] × [−2 −1 1 2] | [0.25 0.5 −1 1 −0.5] × [−2 −1 1 2] | one |
| [1 −0.5 0.5 −1] × [1 2 −2 −1] | [−2.5 1 −0.5 0.5 −1] × [1 2 −2 −1] | one |
| [j0.5 −1 1 −j0.5] × [j2 −1 1 −j2] | [(1.25 − j0.5)j0.5 −1 1 −j0.5] × [j2 −1 1 −j2] | one |
| [j −1 −j] × [−j 2 j] | [1j −1 −j] × [−j 2 j] | one |
| [j −1 j] × [−j 2 −j] | [3j −1 j] × [−j 2 −j] | one |
| [j0.5 −1 −j0.5] × [−j 1 j] | [−0.5 j0.5 −1 −j0.5] × [−j 1 j] | one |
| [j0.5 −1 j0.5] × [j −1 j] | [1.5 j0.5 −1 j0.5] × [j −1 j] | one |
| [0.5 −1 0.5 0.5 −1 0.5] × [1 1 1 1 1 1] | [0.5 0.5 −1 0.5 0.5 −1 0.5] × [1 1 1 1 1 1] | one |
| [−0.5 1 −0.5 0.5 −1 0.5] × [1 1 1 −1 −1 −1] | [−1.5 −0.5 1 −0.5 0.5 −1 0.5] × [1 1 1 −1 −1 −1] | one |
| [−0.5 0.5 1 −1 −0.5 0.5] × [1 −1 1 −1 1 −1] | [0.5 −0.5 0.5 1 −1 −0.5 0.5] × [1 −1 1 −1 1 −1] | one |

Additional Pulses Incorporating Subapertures

The selection of the amplitude and phase for an extra reverberation-suppression pulse(s) is described above, but further selection of a subaperture is preferred if subgroups of elements, or subapertures, are used in the multiple-pulse Examples of sequences that incorporate subapertures to reduce pressure levels at contrast agent sites include, but are not limited to, the examples of Table 2. As before, the reverberation-suppression pulses are shown in boldface type.

TABLE 2

| Multiple-Pulse Sequence | Improved Sequence | Number of Additional Pulses |
|---|---|---|
| [1a -(1a + 1b) 1] × [1 1 1] | [1b 1a -(1a + 1b) 1] × [1 1 1] | one |
| [1a (1a + 1b) 1b] × [1 −1 1] | [−1b 1a (1a + 1b) 1b] × [1 −1 1] | one |
| [1a -(1a + 1b) 1b] × [1 1 1] | [-(1a + 1b) 1b 1a -(1a + 1b) 1b] × [1 1 1] | two |
| [1a (1a + 1b) 1b] × [1 −1 1] | [-(1a + 1b) −1b 1a (1a + 1b) 1b] × [1 −1 1] | two |
| [(1a + 1b) −1a 1b -(1a + 1b)] × [1 2 −2 −1] | [(−4a − 1b) (1a + 1b) −1a 1b -(1a + 1b)] × [1 2 −2 −1] | one |
| [j1a -(1a + 1b) −j1b] × [−j 1 j] | [−1bj 1a -(1a + 1b) −j1b] × [−j 1 j] | one |
| [1a -(1a + 1b) 1b 1a -(1a + 1b) 1b] × [1 1 1 1 1 1] | [1b 1a -(1a + 1b) 1b 1a -(1a + 1b) 1b] × [1 1 1 1 1 1] | one |
| [−1a 1b(1a + 1b) -(1a + 1b) −1a 1b] × [1 −1 1 −1 1 −1] | [1b −1a 1b (1a + 1b) -(1a + 1b) −1a 1b] × [1 −1 1 −1 1 −1] | one |
| [j1a -(1a + 1b) j1b] | [(2a + 1b) j1a -(1a + 1b) j1b] × [j −1 j] | one |

In Table 2, $1a$ and $1b$ are subapertures with amplitudes 1 which together combine to form a full aperture. Of course, the use of different transmit voltages and the use of more than two subapertures to achieve desired pressure levels can be combined together to achieve a desired multiple-pulse sequence for detecting one or more harmonic signal orders.

Additional Pulses for Interleaved Sequences

To improve the detectability of slowly moving contrast agents the contrast-to-tissue specificity generated by detecting harmonics can be further improved by detecting motion between two or more received pulses. If the desired scanning depth is used to determine the time between sequential transmit events, the minimum detectable motion of contrast agent can be limited, or suboptimal, since the weighted combination of multiple pulses acts as a filter that suppresses signals that originate from areas without motion and from areas with little motion. Small displacements of contrast agent between two or more transmit events can be more effectively detected by increasing the time between transmit events; however, this reduces frame rates. One method used to avoid the loss in frame rate is to interleave groups of multiple-pulse sequences. For example, to double the time between transmit events for any two pulses within one desired pulse sequence, an additional sequence can be generated on an adjacent line. Thus, for the example with a sequence of [1 2 1]×[1 −1 1], the sequence would be as follows:

transmit pulses: $(1)_1 (1)_2 (2)_1 (2)_2 (1)_1 (1)_2$, receive weights: $(1)_1 (1)_2 (-1)_1 (-1)_2 (1)_1 (1)_2$, where the subscripts 1 and 2 correspond to different lines used to form an image. With this method the desired multiple-pulse sequence [1 2 1]×[1 −1 1] is preserved on each line, but the time between any two pulses is doubled. This example can be extended to more general sequences with more or less than three pulses and where the contrast-pulse-sequence-interleave-ratio (CPSIR) is greater than one. For this specific example the CPSIR is 2.

To adequately suppress acoustic reverberations, the amplitude, phase, and subaperture (if subapertures are used) of the additional pulses are chosen correctly and transmitted on the correct acoustic line(s). As an example, for the three pulse sequence [1 −2 1]×[1 1 1] with a CPSIR of 3, an additional transmit event with amplitude 1 can be transmitted on the third line. The sequentially transmitted pulses for three unique acoustic lines are preferably as shown in Table 3.

TABLE 3

| Line No. 1 | Line No. 2 | Line No. 3 |
|---|---|---|
|  |  | T1 |
| T2 | T3 | T4 |
| T5 | T6 | T7 |
| T8 | T9 | T10 |

In Table 3, T1, T2, T3, T4, T8, T9 and T10 are equal to 1 in amplitude, and T5, T6, and T7 are equal to −2 in amplitude. Since reverberant energy resulting from the transmitted signal T4 on line 3 interferes with the received signal after signal T5 is transmitted on line 1, a reverberation-suppression pulse T1 should be transmitted on line 3 with an amplitude and phase equal to that of the value Z defined earlier. If more than one additional pulse is used, this concept can be easily extended. For this specific example, if two additional transmit events are used, the first additional pulse is transmitted on the second line before the transmit event corresponding to T1 on the third line. If subaperture combinations are incorporated, the appropriate subapertures are used. For example, if the pulses T2, T3 and T4 incorporate a subaperture b and the pulses T8, T9, and T10 incorporate a subaperture a, where the addition of subaperture a and b defines the full aperture used for the pulses T5, T6, and T7, then the additional one pulse or two pulses preferably incorporate the subaperture a.

Method 2:
Modified Sequences Across Lines

Additional transmit events can be avoided for some sequences if the amplitude and/or phase can be modified for each pulse in a multiple-pulse sequence without affecting the suppression of fundamental energy. One example for the pulse sequence [1 2 1]×[1 −1 1] is shown in Table 4 utilizing the same convention adopted above with a CPSIR of 1.

TABLE 4

| Line No. 1 | Line No. 2 | Line No. 3 | Line No. 4 | Line No. 5 |
|---|---|---|---|---|
| 1 | −1 | 1 | −1 | . . . |
| 2 | −2 | 2 | −2 | . . . |
| 1 | −1 | 1 | −1 | . . . |

With this approach, inverting the polarity of all three pulses in a sequence on alternating lines generates the desired suppression of fundamental energy and preservation of second and third order harmonics. If adequate fundamental suppression is obtained by utilizing the last firing of a previous line, additional pulses are not required on each line, maintaining high frame rates.

This approach can be extended further to incorporate sequences that use a CPSIR greater than 1. For the same desired pulse sequence per line as shown above, the two additional pulses of Table 5 can be used to suppress acoustic reverberations from one and two preceding transmit events seen during the reception of signals from a current transmit event. In the example of Table 5, the CPSIR is 4.

TABLE 5

| Line No. 1 | Line No. 2 | Line No. 3 | Line No. 4 |
|---|---|---|---|
|  |  | −1 | 1 |
| 1 | −1 | 1 | −1 |
| 2 | −2 | 2 | −2 |
| 1 | −1 | 1 | −1 |

As used herein, the following conventions have been used in defining transmit pulse amplitude and phase, and receive weight. In transmit pulse sequences, the stated numbers indicate the amplitude of the pulse, and the following convention is used for phase: a positive polarity indicates a phase of 0°, a negative polarity indicates a phase of 180°, a phase j indicates a phase of 90°, and a phase −j indicates a phase of 270°. With respect to receive weights, a positive polarity indicates that the associated receive signal is to be summed and a negative polarity indicates that the associated receive signal is to be subtracted. An imaginary receive weight such as j or −j indicates a phase of 90° or −90°, respectively, generated by a complex filter. The same conventions are used in U.S. patent Ser. No. 09/514,803, which should be consulted for further details.

It should be apparent from the foregoing that an improved method has been described that suppresses reverberation in the combined signal generated from a multiple-pulse sequence of transmit pulses that differ in at least one of amplitude and phase.

Many alternatives are possible. For example, instead of transmitting all transmit pulses and receiving all receive signals for a given multiple-pulse sequence along a single acoustic line, as described above, the transmit pulses and/or the receive signals for a single multiple-pulse sequence may be steered in more than one direction. See, for example, the alternate line phasing techniques described in U.S. patent application Ser. No. 09/282,396, filed Mar. 31, 1999, assigned to the assignee of the present invention and hereby incorporated by reference.

As used herein, the term "set" is used broadly to signify two or more.

The term "immediately prior to" is used in connection with reverberations, and one pulse is said to be transmitted immediately prior to another pulse if reverberations from the one pulse have not died out at the time the other pulse is transmitted.

The foregoing detailed description has discussed only a few of the many forms that this invention can take. For this reason, this detailed description is intended by way illustration and not limitation. It is only the following claims, including all equivalents, that are intended to define the scope of this invention.

We claim:

1. A medical ultrasonic imaging method comprising:

(a) transmitting a set of ultrasonic pulses, said set comprising at least two ultrasonic pulses that differ in at least one of amplitude and phase;

(b) acquiring a set of receive signals in response to the set of ultrasonic pulses;

(c) combining the set of receive signals; and (d) transmitting at least one reverberation-suppression pulse immediately prior to (a), each reverberation-suppression pulse characterized by an amplitude and phase selected to suppress acoustic reverberations in the combined first set of receive signals.

2. The method of claim 1 wherein the set of ultrasonic pulses comprises a first pulse, and wherein the first pulse differs from each reverberation-suppression pulse in at least one of amplitude and phase.

3. The method of claim 1 wherein (d) comprises transmitting a single reverberation-suppression pulse.

4. The method of claim 1 wherein (d) comprises transmitting two reverberation-suppression pulses.

5. The method of claim 1 wherein each reverberation-suppression pulse is included in an additional set of ultrasonic pulses, said additional set comprising at least two ultrasonic pulses that differ in at least one of amplitude and phase, and wherein the method further comprises:

(e) acquiring an additional set of receive signals in response to the additional set of ultrasonic pulses; and (f) combining the additional set of receive signals.

6. The method of claim 5 wherein the ultrasonic pulses of (a) are steered along a first steering direction, and wherein the ultrasonic pulses of the additional set are steered along a second steering direction, different from the first steering direction.

7. The method of claim 6 wherein the first and second steering directions are aligned with respective adjacent acoustic lines.

8. The method of claim 5 wherein the ultrasonic pulse of (a) and the ultrasonic pulses of the additional set are steered along a common steering direction.

9. The method of claim 1 wherein the ultrasonic pulses of (a) are steered along a first steering direction.

10. The method of claim 5 wherein (e) is performed before (b).

11. The method of claim 1 wherein the combining act of (c) is operative to suppress at least one component selected from the group consisting of: a fundamental component, a second harmonic component, and a third harmonic component.

12. The method of claim 1 wherein the set of ultrasonic pulses comprises a first pulse transmitted in (a) with a first transducer aperture, and wherein said reverberation-suppression pulse is transmitted in (d) with a second transducer aperture, different from the first transducer aperture.

* * * * *